United States Patent
Drabarek et al.

(10) Patent No.: US 6,462,815 B1
(45) Date of Patent: Oct. 8, 2002

(54) DEVICE FOR OPTICALLY TESTING SURFACES

(75) Inventors: Pawel Drabarek, Tiefenbronn (DE); Rolf Ofen, Oberhaid (DE); Goetz Kuehnle, Hemmingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/402,687

(22) PCT Filed: Apr. 3, 1998

(86) PCT No.: PCT/DE98/00950

§ 371 (c)(1),
(2), (4) Date: Jan. 1, 2000

(87) PCT Pub. No.: WO98/45689

PCT Pub. Date: Oct. 15, 1998

(30) Foreign Application Priority Data

Apr. 7, 1997 (DE) .......................................... 197 14 202

(51) Int. Cl.$^7$ .............................................. G01N 21/00
(52) U.S. Cl. ............................. 356/241.1; 356/237.2; 356/239.2
(58) Field of Search .......................... 356/241.1, 243.4, 356/237.1, 237.2, 239.2, 369, 376, 237.3, 352, 358, 359, 360, 450, 451, 432, 124; 250/559.27, 227

(56) References Cited

U.S. PATENT DOCUMENTS

| | | | | |
|---|---|---|---|---|
| 4,055,382 A | * | 10/1977 | Ziekman et al. | 356/241.1 |
| 4,197,007 A | * | 4/1980 | Costa et al. | 356/432 |
| 4,225,240 A | * | 9/1980 | Balasubramanian | 356/360 |
| 4,355,904 A | * | 10/1982 | Balasubramanian | 356/376 |
| 4,601,575 A | * | 7/1986 | Tamaki | 356/124 |
| 4,709,145 A | * | 11/1987 | Spillman, Jr. | 250/227 |
| 4,725,144 A | * | 2/1988 | Nelson et al. | 356/360 |
| 4,874,246 A | * | 10/1989 | Den Boef | 356/375 |
| 4,963,018 A | * | 10/1990 | West | 356/214.1 |
| 4,967,092 A | * | 10/1990 | Fraignier et al. | 356/241.1 |
| 5,110,211 A | * | 5/1992 | Niki et al. | 356/345 |
| 5,189,489 A | * | 2/1993 | Brunfeld | 356/358 |
| 5,210,591 A | * | 5/1993 | DeGroot | 356/357 |
| 5,270,790 A | * | 12/1993 | Matsummura | 356/346 |
| 5,321,497 A | * | 6/1994 | Ai et al. | 356/359 |
| 5,381,225 A | | 1/1995 | Kohno | |
| 5,706,085 A | * | 1/1998 | Blossey et al. | 356/357 |
| 5,963,316 A | * | 10/1999 | Miura et al. | 356/237.3 |

FOREIGN PATENT DOCUMENTS

| | | |
|---|---|---|
| DE | 32 32 904 | 3/1984 |
| DE | 42 06 609 | 9/1993 |
| EP | 0 267 705 | 5/1988 |
| GB | 2 126 715 | 3/1984 |
| JP | 58 223113 | 12/1983 |

\* cited by examiner

Primary Examiner—Frank G. Font
Assistant Examiner—Sang H. Nguyen
(74) Attorney, Agent, or Firm—Kenyon & Kenyon

(57) ABSTRACT

A device for inspecting surfaces includes a beam splitter which couples out, from an input radiation a first measuring radiation and a second measuring radiation. Both measuring radiations exhibit different properties. A first exemplary embodiment makes provision for the different property to be achieved by different polarization planes. Another exemplary embodiment makes provision for the different properties to be achieved by different wavelengths. The measuring radiations reflected by the surfaces are brought together by the beam splitter to form an output radiation which is fed to an optical receiving device. The device according to the present invention is mainly suited for inspecting surfaces in bores, especially, in blind-end bores.

13 Claims, 2 Drawing Sheets

DEVICE FOR OPTICALLY TESTING SURFACES

FIELD OF THE INVENTION

The present invention relates to a device for optically inspecting surfaces.

BACKGROUND INFORMATION

German Published Patent Application No. 32 32 904 describes a device in which where a laser radiation is directed toward a surface to be inspected within a bore in a workpiece, and in which the radiation reflected by the surface is altered as a function of the surface properties. An input radiation is conducted toward a mirror by a central optical waveguide, the mirror deflecting the input radiation by approximately 90° toward the wall of the bore. The radiation reflected by the surface is guided out of the bore, on one hand, by the central optical waveguide, and, on the other hand, by further optical waveguides concentrically arranged around the central optical waveguide. Between the central optical waveguide and the further optical waveguides, provision is made for an optical dead zone. Thus, the device enables in a simple manner a concurrent measurement both in the bright and the dark field of the radiation reflected by the surface.

SUMMARY OF THE INVENTION

An object of the present invention is to specify a device for optically inspecting surfaces which has a simple design. The device according to the present invention has an advantage that a first and at least a second surface can be inspected at the same time. Apart from the individual determination of measuring results, a comparative measurement between the two surfaces to be inspected is possible without having to move the device for that purpose.

According to the present invention, provision is made for a beam splitter to couple out, from an input radiation, a first measuring radiation directed toward the first surface to be inspected, and a second measuring radiation directed toward the second surface to be inspected. In the beam splitter, the measuring radiations reflected by the surfaces are brought together again to form an output radiation which is conducted toward a measuring device which measures the two measuring radiations separately. The two measuring radiations have different properties which enable a separate evaluation in the measuring device.

The device according to the present invention is particularly suited for inspecting surfaces in bores, especially, in blind-end bores. The simple design of the device according to the present invention enables the inspecting of surfaces in bores having a small bore diameter. A separate evaluation of the measuring radiations contained in the output radiation enables, for example, the determination of the straightness or the roundness of the bore. Since, moreover, the measuring results of both surfaces are available coincidently, it is possible to determine, for example, the alignment of the bore.

A first embodiment according to the present invention makes provision for different polarization planes as properties of the measuring radiations.

Preferably, the different polarization planes are achieved by designing the beam splitter as a polarization beam splitter. Suitable input radiation includes, for example, a nonpolarized or a circularly polarized radiation. Instead of the polarization beam splitter, it is also possible to use a conventional beam splitter, downstream of which polarization filters are arranged in the beam paths of the two measuring radiations, respectively.

One embodiment according to the present invention provides for already polarizing the input radiation in a predefined polarization plane. By changing the polarization plane, for example, by using a polarization rotator, it is possible to inspect the two surfaces consecutively. In this embodiment, the measuring device can be implemented in a particularly simple manner, since the output radiation corresponds to either the first or the second reflected measuring radiation. A signal which controls the polarization rotator assumes the association of the acquired signal with the respective reflected measuring radiation in the measuring device.

Another embodiment according to the present invention provides for the different properties of the measuring radiations to be selected using different wavelengths. The input radiation contains two portions of radiation having different wavelengths, wavelength-selective filters being arranged in the beam path of the first and of the second measuring radiation, respectively. Provided that the input radiation contains both portions of radiation coincidently, it is possible to measure the reflected measuring radiations simultaneously in the measuring device using appropriate wavelength-selective filters. Provided that the input radiation has sequentially different wavelengths, a measuring device is sufficient which measures the output radiation independently of the wavelength.

Another advantageous embodiment according to the present invention provides for the beam splitter to couple out the first measuring radiation at an angle of at least approximately 90° with respect to the direction of the input radiation, and to let the second measuring radiation pass essentially without a change in direction.

A further advantageous embodiment according to the present invention provides for a beam deflector to be arranged in the beam path of the second measuring radiation so as to deflect the beam path in a different direction. Provided that the change in direction is at least approximately 90°, the two surfaces to be inspected can be located in one plane. Thus, it is possible to judge a bore at different bore depths at the same time.

DETAILED DESCRIPTION

Figure 1:
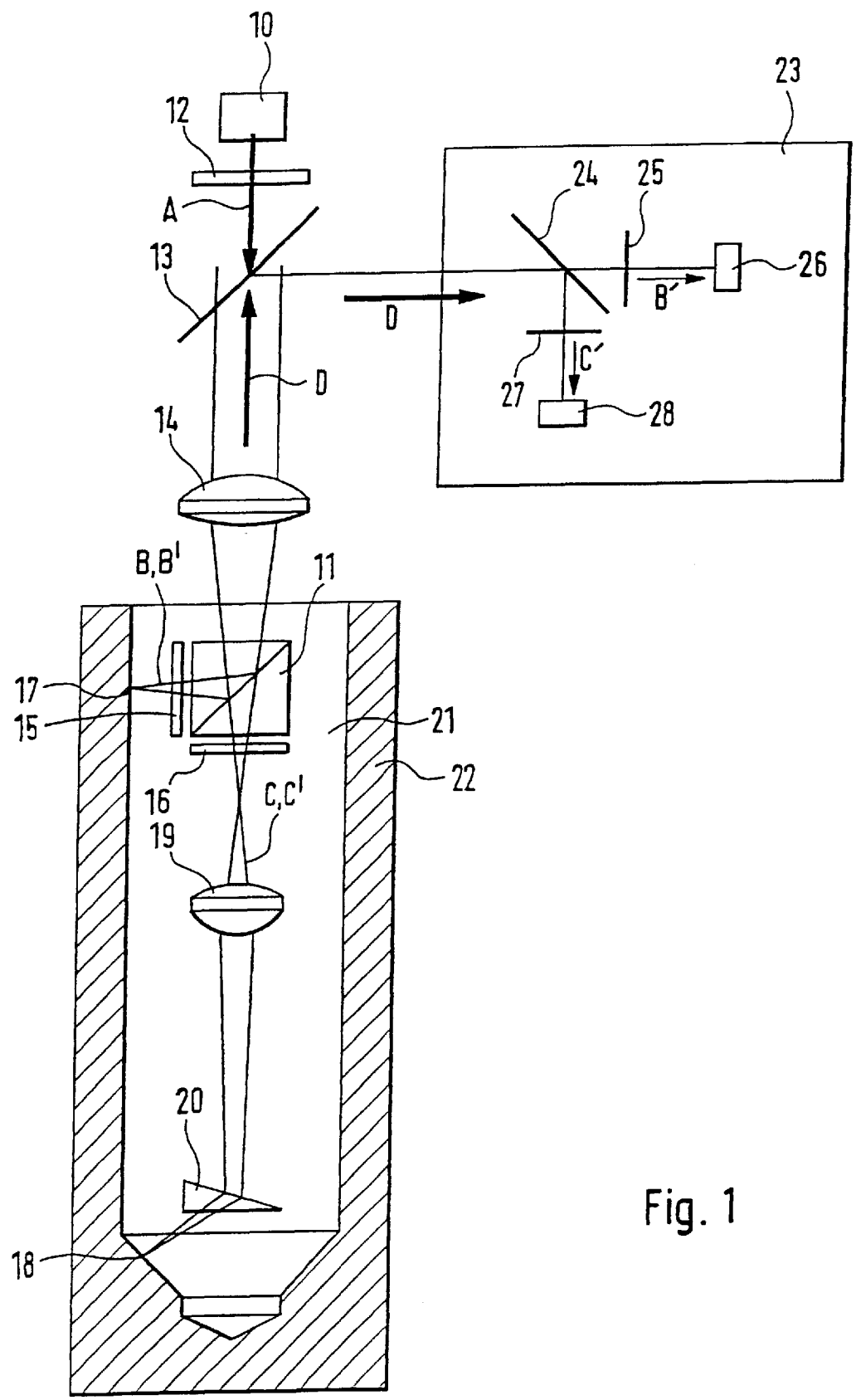
FIG. 1 illustrates a first embodiment of a device according to the present invention.

FIG. 1 shows a radiation source 10 which emits an input radiation A in a direction toward a beam splitter 11. Arranged in the beam path between radiation source 10 and beam splitter 11 are a polarization rotator 12, a first semi-transparent mirror 13 as well as a first lens 14. Beam splitter 11 couples out a first measuring radiation B as well as a second measuring radiation C from input radiation A. Arranged in the beam path of first measuring radiation B is a first polarizer 15, and a second polarizer 16 is arranged in the beam path of second measuring radiation C. First measuring radiation B impinges upon a first surface 17 to be inspected, and second measuring radiation C impinges upon a second surface 18 to be inspected. Arranged in the beam path of second measuring radiation C are a second lens 19 as well as a beam deflector 20. Surfaces 17, 18 to be inspected are surface parts of a bore 21 in a workpiece 22. Measuring radiations B', C' reflected by surfaces 17, 18 to be inspected are united by beam splitter 11 to form an output radiation D which is coupled out toward an optical receiving device 23 by first semitransparent mirror 13.

Optical receiving device 23 contains a second semitransparent mirror 24 which couples out the reflected first measuring radiation B' and the reflected second measuring radiation C' from output radiation D. Reflected first measuring radiation B' passes through third polarizer 25 and impinges upon a first radiation receptor 26. Reflected second measuring radiation C', after passing a fourth polarizer 27, reaches a second radiation receptor 28.

The device according to the present invention functions in accordance with FIG. 1 as follows:

Beam splitter 11 couples out first and second measuring radiations B, C from input radiation A provided by radiation source 10. The two measuring radiations B, C exhibit different properties which, in accordance with the exemplary embodiment illustrated in FIG. 1, have different polarization planes. Even without further measures, a polarization occurs as a function of the refractive indices of the materials used in beam splitter 11, and as a function of the angular relations. A complete polarization is achieved by implementing beam splitter 11 as a polarization beam splitter. A different measure according to the present invention provides for arranging polarizers 15, 16 in the beam paths of the two measuring radiations B, C.

First lens 14, which is arranged in the beam path of input radiation A, allows first measuring radiation B to be focussed on first surface 17 to be inspected. With the assistance of the second lens 19, which is arranged in the beam path of second measuring radiation C, it is also possible to focus second measuring radiation C on second surface 18 to be inspected.

In the embodiment shown, in FIG. 1 beam splitter 11 couples out first measuring radiation B from input radiation A at an angle of at least approximately 90° with respect to the direction of input radiation A while second measuring radiation C is in the direction of input radiation A. Beam deflector 20 permits a further deflection of second measuring radiation C. It is also possible to make provision for a deflection or at least approximately 90° which will allow the two measuring radiations B, C to run substantially parallel to each other. Using this measure, surfaces 17, 18 to be inspected are spaced from each other and may be disposed in the same plane so that, for example, the alignment of the bore can be measured. In the embodiment illustrated in FIG. 1, beam deflector 20 deflects second measuring radiation C by an angle of approximately 45° which will allow surfaces to be inspected which are not disposed in one plane.

Measuring radiations B, C impinging on surfaces 17, 18 to be inspected are partially reflected and partially scattered as a function of the surface properties. There appears always a portion of reflected measuring radiation B', C' which has the opposite direction of incident measuring radiation B, C. Reflected measuring radiations B', C' are united by beam splitter 11 to form output radiation D.

First semitransparent mirror 13 couples out output radiation D and conducts it to optical receiving device 23. In a specific embodiment according to the present invention, optical receiving device 23 contains just first radiation receptor 26 which measures output radiation D. Optical receiving device 23 can have this simple design provided that the two measuring radiations B, C exhibit the different properties sequentially. Such an implementation is possible by using polarization rotator 12 to polarize, in any planes, the radiation emitted by radiation source 10. Since input radiation A has already been polarized, beam splitter 11 can, in each case, couple out only that measuring radiation B, C which already exhibits the right polarization. By rotating the polarization plane, it is possible to provide exclusively first measuring radiation B or exclusively second measuring radiation C. By rotating the polarization plane, however, it is also possible to provide an arbitrary ratio of concurrently appearing measuring radiations B, C. If the information about the polarization of input radiation A is known, the signal which is emitted by the only radiation receptor can unequivocally be associated with surfaces 17, 18 to be inspected, respectively.

The refinement of optical measuring device 23 shown in FIG. 1 allows reflected measuring radiations B', C' to be measured simultaneously. Second semitransparent mirror 24 divides output radiation D into two beam components. Arranged in the paths of the two beam components are polarizers 25, 27 which couple out desired reflected measuring radiations B', C' from output radiation D. Semitransparent mirror 24 and the two polarizers 25, 27 can be replaced with a polarization beam splitter. Reflected measuring radiations B', C' are received separately by first and second radiation receptor 26, 28 and made available as output signals. The signals provided by the two radiation receptors 26, 28 are fed to a further evaluation circuit not shown which provides measuring results from the individual signals or from combinations of both signals, the measuring results allowing conclusions about the properties of surfaces 17, 18 to be inspected. Detailed information on which data can be obtained about the surface can be gathered from the above identified reference.

Figure 2:
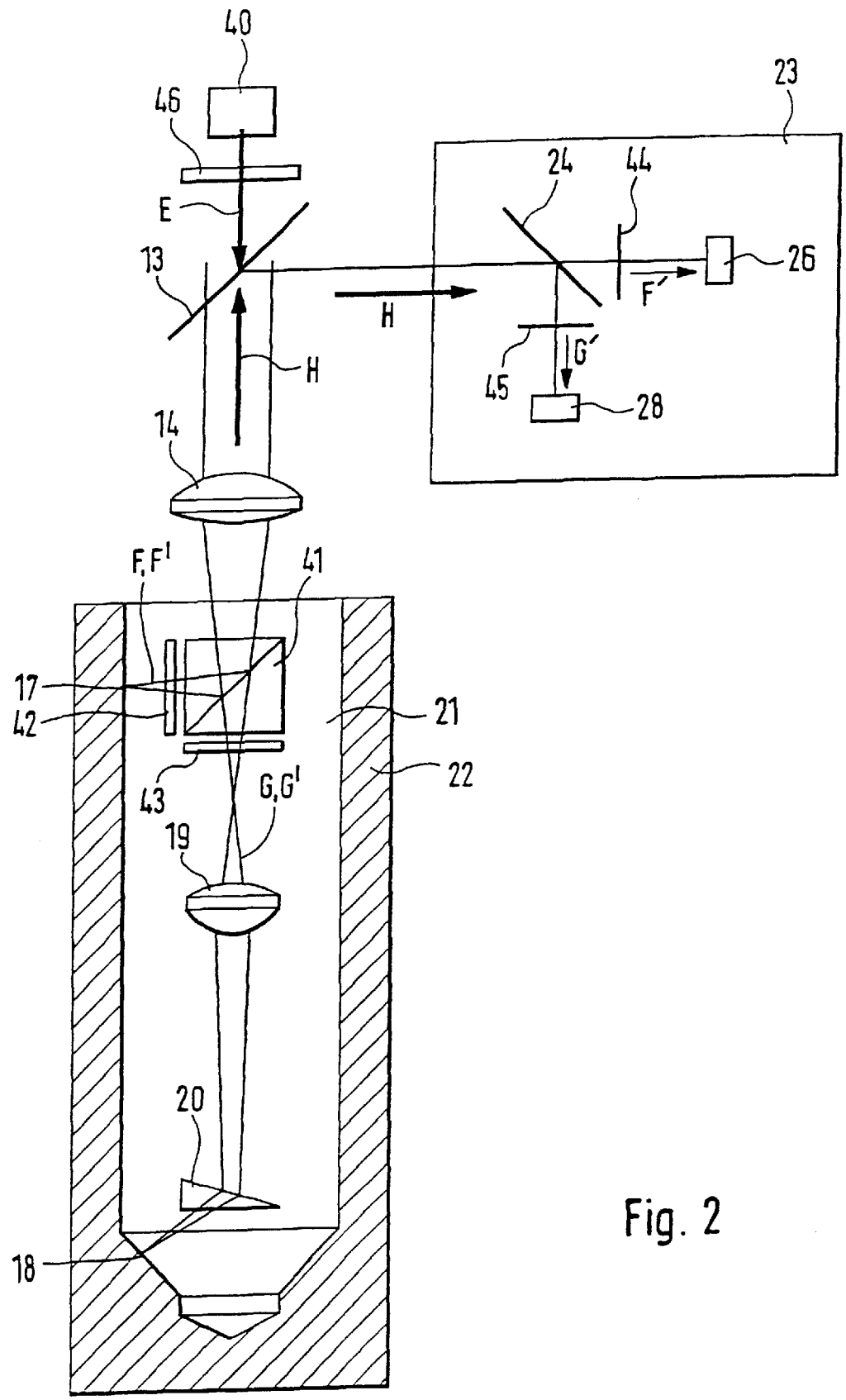
FIG. 2 illustrates a second embodiment of the device according to the present invention.

FIG. 2 shows another exemplary embodiment of the device for inspecting surfaces according to the present invention. Those parts shown in FIG. 2 which correspond to the parts shown in FIG. 1 bear identical reference symbols.

A beam splitter 41 couples out a first measuring radiation F as well as a second measuring radiation G from an input radiation E provided by a radiation source 40. Arranged in the beam path of first measuring radiation F is a first wavelength-selective filter 42, and a second wavelength-selective filter 43 is arranged in the beam path of second measuring radiation G.

Measuring radiations F', G' reflected by the surfaces 17, 18 are united by beam splitter 41 to form output radiation H.

Optical receiving device 23 includes second semitransparent mirror 24 which divides output radiation H into two beam components. Intended to appear in the first beam component is first reflected measuring radiation F' which is filtered out from output radiation H by a third wavelength-selective filter 44. Intended to appear in the other beam path is second reflected measuring radiation G' which is filtered out from output radiation H by a fourth wavelength-selective filter 45.

Arranged in the beam path of input radiation E is a selective filter bank 46.

The device shown in FIG. 2 works as follows:

The fundamental difference between the exemplary embodiments of the device according to the present invention shown in FIG. 1 and FIG. 2 lies in that, in place of the polarization plane establishing the different properties in measuring radiations B, C, now the different properties are established by different wavelengths of the two measuring radiations F, G.

The polarizing properties of beam splitter 11 shown in FIG. 1 do not matter in the case of beam splitter 41 shown in FIG. 2. The purpose of beam splitter 41 is just to couple out portions of radiation from input radiation E.

The wavelength selection is carried out in first measuring radiation F by first wavelength-selective filter 42, and in second measuring radiation G by second wavelength-selective filter 43 arranged there. In the embodiment illustrated in to FIG. 2, as in the embodiment of the device according to the present invention explained on the basis of FIG. 1, it is also possible that input radiation E is provided by radiation source 40 in such a manner that both different properties are contained in both measuring radiations F, G at the same time. In the present case, input radiation E then contains portions of radiation having both wavelengths to which the two wavelength-selective filters 42, 43 are matched. Equally, it is possible for input radiation E again to exhibit the different property in a chronological sequence. For the implementation, provision is made, for example, for selective filter bank 46 shown in FIG. 2, which, by switching, provides that input radiation E has, in each case, only one predetermined wavelength.

The equivalent applies to optical receiving device 23, which has one radiation receptor in the case of a chronological sequence of different wavelengths in output radiation H, wavelength-selective filters not being required. If it is required to evaluate the two reflected measuring radiations F', G' simultaneously, a separation by different wavelenghts must be carried out. The third wavelength-selective filter contained in optical receiving device 23 couples out first reflected measuring radiation F', and fourth wavelength-selective filter 45 couples out second reflected measuring radiation G'.

The two reflected measuring radiations F', G' are converted by the two radiation receptors 26, 28 into signals which are further processed in the manner described earlier.

What is claimed is:

1. A device for optically inspecting a plurality of surfaces, the plurality of surfaces including at least a first surface and a second surface, the first surface differing from the second surface, the device comprising:

a beam splitter for splitting an input radiation in to a first measuring radiation and a second measuring radiation, the first measuring radiation being directed toward and being reflected by the first surface as a first reflected measuring radiation, the second measuring radiation being directed toward and being reflected by the second surface as a second reflected measuring radiation, and the first measuring radiation exhibiting a first property that differs from a second property exhibited by the second measuring radiation, and the beam splitter combining the first reflected measuring radiation and the second reflected measuring radiation into an output radiation;

a first radiation receptor;

a second radiation receptor; and an optical measuring device having a semitransparent mirror, the optical measuring device receiving the output radiation, and the semitransparent mirror in the optical measuring device directing the first reflected measuring radiation of the output radiation toward the first radiation receptor and directing the second reflected measuring radiation of the output radiation toward the second radiation receptor.

2. The device according to claim 1, wherein the first property corresponds to a first polarization plane, and wherein the second property corresponds to a second polarization plane, the first polarization plane being different from the second polarization plane.

3. The device according to claim 2, wherein the beam splitter is a polarization beam splitter.

4. The device according to claim 2, further comprising:

a first polarization filter disposed between the beam splitter and the first surface; and a second polarization filter disposed between the beam splitter and the second surface.

5. The device according to claim 1, wherein the input radiation is polarized.

6. The device according to claim 1, wherein the first property corresponds to a first wavelength, and wherein the second property corresponds to a second wavelength, the first wavelength being different from the second wavelength.

7. The device according to claim 1, wherein the beam splitter directs the first measuring radiation at an angle with respect to the input radiation, the angle being at least approximately 90 degrees, and wherein the beam splitter directs the second measuring radiation in a direction substantially the same as a direction of the input radiation.

8. The device according to claim 1, further comprising:

a beam deflector disposed in a beam path of the second measuring radiation.

9. The device according to claim 8, wherein the beam deflector deflects the second measuring radiation at an angle, the angle being at least approximately 90 degrees.

10. The device according to claim 1, further comprising:

a first lens disposed in a beam path of the input radiation; and a second lens disposed in a beam path of the second measuring radiation.

11. The device according to claim 1, wherein the optical measuring device includes a polarization beam splitter, the polarization beam splitter separating the first reflected measuring radiation from the output radiation and separating the second reflected measuring radiation from the output radiation.

12. The device according to claim 1, wherein the optical measuring device includes a third polarizer and a fourth polarizer, the third polarizer coupling out the first reflected measuring radiation from the output radiation, and the fourth polarizer coupling out the second reflected measuring radiation from the output radiation.

13. The device according to claim 1, wherein the optical measuring device includes a third wavelength-selective filter and a fourth wavelength-selective filter, the third wavelength-selective filter coupling out the first reflected measuring radiation from the output radiation, and the fourth wavelength-selective filter coupling out the second reflected measuring radiation from the output radiation.

* * * * *